| United States Patent [19] | | | [11] | 3,962,304 |
|---|---|---|---|---|
| Matsushima et al. | | | [45] | June 8, 1976 |

[54] ALKOXY-SUBSTITUTED BENZYL DITHIOCARBAMIC ACID ESTERS

[75] Inventors: Kiyoshi Matsushima; Masao Miyamoto; Nobuo Fukazawa, all of Tokyo, Japan

[73] Assignee: Bayer Aktiengesellschaft, Leverkusen, Germany

[22] Filed: Dec. 11, 1969

[21] Appl. No.: 884,321

[30] Foreign Application Priority Data
Dec. 20, 1968    Japan.................................. 43-93912

[52] U.S. Cl.............................. 260/455 A; 71/101; 71/DIG. 1
[51] Int. Cl.².......................................... C07C 155/08
[58] Field of Search.................. 260/455 A; 71/101; 424/300

[56] References Cited
UNITED STATES PATENTS

| 2,972,627 | 2/1961 | Garmaise et al.................... 424/300 |
|---|---|---|
| 2,992,091 | 7/1961 | Harman et al.................. 260/455 A |
| 3,075,875 | 1/1963 | Margot............................... 424/300 |
| 3,532,488 | 10/1970 | Husted et al..................... 260/455 A |
| 3,647,850 | 3/1972 | Ono et al......................... 260/455 A |

FOREIGN PATENTS OR APPLICATIONS

| 1,493,102 | 7/1967 | France............................ 260/455 A |
|---|---|---|
| 201,380 | 11/1967 | U.S.S.R........................... 260/455 A |

OTHER PUBLICATIONS

Mel'nikov et al., "Organic insectofungicides etc.," (1968) CA 69 No. 51760e (1968).

*Primary Examiner*—Glennon H. Hollrah
*Attorney, Agent, or Firm*—Burgess, Dinklage & Sprung

[57] ABSTRACT

Alkoxy-substituted benzyl dithiocarbamic acid esters, i.e. [(optionally mono- and di- alkyl, alkoxy, nitro, chloro and bromo substituted)-(alkoxy substituted)-benzyl]-dithiocarbamates, which possess herbicidal properties and which may be produced by conventional methods.

5 Claims, No Drawings

ALKOXY-SUBSTITUTED BENZYL DITHIOCARBAMIC ACID ESTERS

The present invention relates to and has for its objects the provision for particular new alkoxy-substituted benzyl dithiocarbamic acid esters, i.e. [(optionally mono- and di- alkyl, alkoxy, nitro, chloro and bromo substituted)-(alkoxy substituted)-benzyl]-dithiocarbamates, which possess herbicidal properties, active compositions in the form of mixtures of such compounds with solid and liquid dispersible carrier vehicles, and methods for producing such compounds and for using such compounds in a new way, especially for combating weeds, undesired plants, and the like, with other and further objects becoming apparent from a study of the within specification and accompanying examples.

It is already known that benzyl-N,N-dimethyl-dithiocarbamate (A), pentachloro-phenol (B), which may be designated as PCP, and 2-methyl-4-chloro-phenoxy acetic acid (C), which may be designated as MCP, possess herbicidal properties.

Hitherto, pentachloro-phenol (PCP) has been used for the control of barnyard grass (*Echinochloa crus-galli*) in paddy fields. However, PCP possesses not only irritant effect on human skin and mucous membranes and thus difficult to formulate safely for agricultural use, but also a specific toxicity to fish and shell-life as well. Accordingly, PCP suffers from drawbacks including limitations as to the time of use and the range of use.

While 2-methyl-4-chloro-phenoxy acetic acid (MCP) has been used for the control of spikerush (*Eleocharis acicularis*), the weed simultaneously growing with barnyard grass in paddy fields, but, this compound is not effective for the control of barnyard grass.

Accordingly, a mixture of the above-mentioned PCP and MCP has been usually used in the past to control simultaneously barnyard grass and spikerush, the main types of weeds in paddy fields.

It has now been found, in accordance with the present invention, that the particular new alkoxy-substituted benzyl dithiocarbamates of the formula

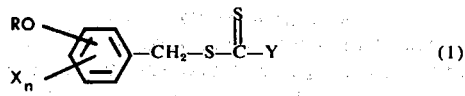

(I)

in which
R is alkyl of 1–4 carbon atoms,
X is alkyl of 1–4 carbon atoms, alkoxy of 1–4 carbon atoms, nitro, chloro or bromo,
n is a whole number from 1 to 2, and
Y is alkylamino having 1–4 carbon atoms in the alkyl moiety or dialkylamino having 1–4 carbon atoms in each alkyl moiety,
exhibit strong herbicidal, especially selective herbicidal, properties.

It has been furthermore found, in accordance with the present invention, that the compounds of formula (I) above may be produced by the process which comprises reacting an alkoxy-substituted benzyl halide of the formula

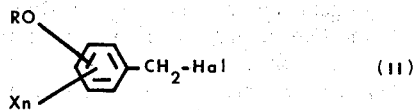

(II)

in which
R, X and n are the same as defined above, and
Hal is a halogen atom such as chloro, bromo, iodo or fluoro, especially chloro,
with a dithiocarbamic acid compound of the formula

(III)

in which
Y is the same as defined above, and
M is hydrogen, or a cation such as an ammonium or alkali metal cation, for example potassium sodium, and the like.

Surprisingly, the particular new compounds according to the present invention show both a higher and more specific herbicidal effectiveness than the previously known compounds which are known to be usable for such purposes, e.g. compounds (A), (B) and (C) above. The instant compounds are especially effective as herbicides for the control of weeds in paddy rice fields, particularly barnyard grass and spikerushes, and exhibit a remarkable effect in killing such weeds, with only slight, if any, phytotoxic effect toward cultivated plants such as rice. The instant compounds therefore represent a valuable contribution to the art.

Advantageously, in accordance with the present invention, in the various formulae herein:
R represents
straight and branched chain lower alkyl hydrocarbon of 1–4 carbon atoms such as methyl, ethyl, n- and iso-propyl, n-, iso-, sec.- and tert.-butyl, and the like, especially $C_{1-3}$ or $C_{1-2}$ alkyl;
X represents
straight and branched chain lower alkyl hydrocarbon of 1–4 carbon atoms such as methyl to tert.-butyl inclusive, and the like, as defined above, especially $C_{1-3}$ or $C_{1-2}$ alkyl;
straight and branched chain lower alkoxy of 1–4 carbon atoms such as methoxy, ethoxy, n- and iso-propoxy, n-, iso-, sec.- and tert.-butoxy, and the like, especially methoxy;
nitro; or chloro;
bromo;
n represents
a whole number from 1 to 2;
such that when $n$ is 1, X is 2-, 3-, 4-, 5- or 6- $C_{1-4}$ alkyl, $C_{1-4}$ alkoxy, nitro, chloro or bromo; and when $n$ is 2, X is 2,3-, 2,4-, 2,5-, 2,6-, 3,4- and 3,5- di $C_{1-4}$ alkyl, $C_{1-4}$ alkoxy, nitro, chloro or bromo, especially dichloro, dimethyl; and
Y represents alkylamino having 1–4 carbon atoms in the alkyl radical such as methyl to tert.-butyl inclusive, and the like, as defined above, -amino, especially $C_{1-3}$ or $C_{1-2}$ alkylamino; or dialkylamino having 1–4 carbon atoms in each alkyl radical such as di (same or mixed) methyl to tert.-butyl inclusive, and the like, as defined above, -amino, especially di $C_{1-3}$ or $C_{1-2}$ (same or mixed) alkylamino.

Preferably, R is $C_{1-3}$ or $C_{1-2}$ alkyl; X is $C_{1-3}$ or $C_{1-2}$ alkyl; or $C_{1-2}$ or $C_1$ alkoxy; or nitro; or chloro; or bromo; $n$ is 1–2; and Y is $C_{1-4}$ alkylamino; or di $C_{1-4}$ alkylamino.

In particular, R is $C_{1-3}$ or $C_{1-2}$ alkyl; $n$ is 1–2; when $n$ is 1 then X is 3- and 5- ($C_{1-3}$ alkyl); or 3-($C_1$ alkoxy); or 3- and 5-nitro; or 3- and 5-chloro; or 3- and 5- bromo; and when $n$ is 2 then X is 3,5- and 3,6-dichloro or 2,6-, 3,5- and 4,5-dimethyl; and Y is $C_{1-4}$ alkylamino; or di $C_{1-4}$ alkylamino.

The reaction course according to the present invention is illustrated by the following reaction formula:

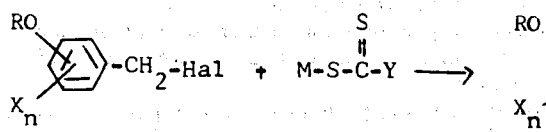 + 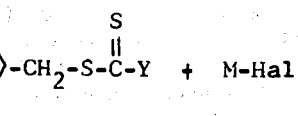 ⟶

(II)                 (III)                          (I)

The starting materials which may be used for the instant production process are clearly characterized by formulae (II) and (III) above, and are well known.

As examples of alkoxy-substituted benzyl halides of formula (II) above which may be used as starting materials, there are mentioned: 2- and 4-(methoxy, ethoxy, n- and iso-propoxy, n-, iso-, sec- and tert.-butoxy)-(optionally appropriately 2-, 3-, 4-, 5- and/or 6-mono and di methyl, ethyl, n- and iso-propyl, n-, iso-, sec.- and tert.-butyl; methoxy; nitro; chloro; or bromo)-benzyl chlorides, bromides, iodides and fluorides, and the like.

As examples of dithiocarbamic acid compounds of formula (III) above which may be used as starting materials, there are mentioned: ammonium, potassium and sodium N-mono and N,N-di (same or mixed) methyl, ethyl, n- and iso-propyl, n-, iso-, sec.- and tert.-butyl -dithiocarbamates, and the corresponding free acids, and the like.

The production process according to the present invention is preferably carried out in the presence of an inert organic solvent (this term includes a mere diluent). Examples of such solvents include aliphatic or aromatic hydrocarbons (which may be halogenated), for example benzine, methylene chloride, chloroform, carbon tetrachloride, benzene, chlorobenzene, toluene, and xylene; ethers, for example diethyl ether, dibutyl ether, dioxan, and tetrahydrofuran; aliphatic alcohols or ketones which have low boiling points, for example methanol, ethanol, acetone, isopropyl ketone, and methyl isobutyl ketone; and the like. Lower aliphatic nitriles, for example acetonitrile, propionitrile, and the like, may also be used.

If M is hydrogen in the appropriate starting compound of formula (III) above, the reaction may preferably be carried out in the presence of an acid-binding agent. Examples of these include alkali metal carbonates and bicarbonates or alcoholates, such as potassium carbonate, sodium bicarbonate, sodium carbonate, or sodium or potassium methylate or ethylate, or aliphatic, aromatic or heterocyclic tertiary bases such as triethylamine, diethyl-aniline, pyridine, and the like. Instead of using an acid-binding agent, a corresponding salt of the free dithiocarbamic acid of formula (III) above may be prepared, e.g. an alkali metal or ammonium salt, and then this salt may be reacted with the starting alkoxy-substituted benzyl halide of formula (II) above.

The reaction according to the instant production process may be carried out within a fairly wide temperature range, but in general at temperatures from substantially between about 30°–110°C, preferably between about 70°–100°C.

In carrying out the production process one may for example proceed as follows.

1 mol of alkali metal or ammonium salt of the dithiocarbamic acid compound of formula (III) above is dissolved in one of the above-noted solvents, preferably methylethyl ketone or acetone, and to the solution of 1 mol of the alkoxy-substituted benzyl halide of formula (II) above is added dropwise, e.g. in the form of a solution in one of said solvents, preferably methylethyl ketone or acetone, and the mixture is heated at 70°–100°C for a short time (e.g. 1–3 hours). Then the mixture is cooled to room temperature, the solid residue filtered off, and the resulting filtrate concentrated under reduced pressure. Upon cooling, the desired product precipitates.

The instant compounds are oils or crystalline substances which are generally not very soluble in water although they are soluble in organic solvents.

Advantageously, the instant active compounds exhibit a strong herbicidal potency and can therefore be used as germination inhibiting agents or weed-killers. By weeds in the sense used herein are meant all plants which grow in places where they are not desired. Whether the active compounds according to the present invention act as total or selective herbicidal agents depends on the amount applied, as the artisan will appreciate.

The active compounds according to the present invention can be used for example in the case of the following plants: dicotyledons, such as mustard (Sinapsis), cress (Lepidium), catch weed (Galium), common chickweed (Stellaria) camomile (Matricaria), French weed (Galinsoga), goose-foot (Chenopodium), stinging nettle (Urtica), groundsel (Senecio), wild amaranth (Amaranthus), common purslane (Portulaca), cotton (Gossypium), beets (Beta), carrots (Daucus), beans (Phaseolus), potatoes (Solanum), coffee (Coffea), cabbage (Brassica), spinach (Spinacia); monocotyledons, such as timothy (Phleum), meadowgrass (Poa), fescue (Festuca), finger grass (Digitaria), goosegrass (Eleusine), green foxtail (Setaria), ryegrass (Lolium), cheat (Bromus), barnyardgrass (Echinochloa), maize (Zea), rice (Oryza), oats (Avena), barley (Hordeum), wheat (Triticum), millet (Panicum) and sugar cane (Saccharum); and the like.

The instant compounds are preferably used as selective herbicides and especially when applied to soil before germination, although they exhibit a particularly good selectivity when applied before and after emergence, e.g. in upland and paddy fields. Such compounds are excellent herbicides for the simultaneous control of barnyard grass and spikerush as well as for the selective control between barnyard grass and rice plants based upon root absorption effect.

Significantly, the active compounds of the present invention are distinguished by the fact that they are not phytotoxic to rice plants although they are markedly effective in small dosages as compared with PCP and MCP, i.e. compounds (B) and (C), etc. which have hitherto been used widely as herbicides in paddy fields. Especially when applied to soil before germination, the instant compounds are far better than the already known herbicides in that such instant compounds show a superior selective herbicidal activity, depending on the amount applied.

The active compounds according to the present invention, because of their properties, can be used during the tilling of paddy fields before the planting of rice, i.e. at a time when suitable control of weeds in rice cultivation heretofore has not been successful.

The active compounds according to the instant invention can be utilized, if desired, in the form of the usual formulations or compositions with conventional inert (i.e. plant compatible or herbicidally inert) pesticide diluents or extenders, i.e. diluents or extenders of the type usable in conventional pesticide formulations or compositions, e.g. conventional pesticide dispersible carrier vehicles, such as solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers including inert organic solvents, such as aromatic hydrocarbons (e.g. benzene, toluene, xylene, dimethyl naphthalene, aromatic naphtha, etc.), halogenated, especially chlorinated, aromatic hydrocarbons (e.g. chlorobenzenes), paraffins (e.g. petroleum fractions), chlorinated aliphatic hydrocarbons (e.g. methylene chloride, etc.), alcohols (e.g. methanol, ethanol, propanol, butanol, etc.), ethers, ether-alcohols (e.g. glycol monomethyl ether, etc.), amines (e.g. ethanol-amine, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, alumina, silica, chalk, i.e. calcium carbonate, talc, kieselguhr, montmorillonite, clay, etc.), and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl aryl-polyglycol ethers, magnesium stearate, sodium oleate, etc.); and/or dispersing agents, such as lignin, sulfite waste liquors, methyl cellulose, etc.

As will be appreciated by the artisan, the active compounds according to the instant invention may be employed alone or in the form of mixtures with one another and/or with such solid and/or liquid dispersible carrier vehicles and/or with other known compatible active agents, especially plant protection agents, such as other herbicides, or fungicides, insecticides, acaricides, nematocides, bactericides, plant growth regulators, soil disinfectants, including phenoxy compounds, chlorophenol compounds, carbamates, diphenyl ethers, ureas, triazine compounds, and other known agricultural chemicals and/or fertilizers, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1 and 95% by weight, and preferably 0.5 and 90% by weight, of the mixture, whereas carrier composition mixtures suitable for direct application or field application generally contemplate those in which the active compound is present in an amount substantially between about 0.005–20%, preferably 0.008–10%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.005–95%, and preferably 0.008–95%, by weight of the mixture.

In particular, the amount of active compound applied per unit area varies according to the purpose intended, i.e. the effect desired, and the mode of application. In general, higher quantities of substantially between about 0–40 kg of active compound per hectare are applied for total or non-selective herbicidal activity, whereas lower quantities of substantially between about 1.25–5 kg of active compound per hectare are applied for selective herbicidal activity, i.e. irrespective of the presence or absence of the carrier vehicle.

The active compounds can also be used in accordance with the well-known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 1 quart/acre, preferably 2–16 fluid ounces/acre, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

While the active compounds can be used particularly effectively according to the pre-emergence method, they are also effective when used according to the post-emergence method.

Especially when application is carried out mainly before the germination of cultivated plants, the general conditions of cultivation are not so important, but the quantity of active compound to be applied per unit area and the application method are important, as the artisan will appreciate.

Furthermore, the present invention contemplates methods of selectively killing, combatting or controlling undesired plants, e.g. weeds and the like, which comprise applying to at least one of (a) such weeds and (b) their habitat, i.e. the locus to be protected, a herbicidally effective or toxic amount of the particular compound of the invention alone or together with a carrier vehicle as noted above. The instant formulations or compositions are applied in the usual manner, for example by spraying, atomizing, scattering, dusting, watering, sprinkling, and the like, whether for pre-emergence application to the soil or postemergence application to the weeds.

It will be realized, of course, that in connection with the pre-emergence use of the instant compounds as well as the post-emergence use thereof, the concentration of the particular active compound utilized in admixture with the carrier vehicle will depend upon the intended application and may be varied within a fairly wide range depending upon the weather conditions, the soil, the purpose for which the active compound is used, e.g. for total or only selective herbicidal effect, and the plants which are to be controlled or protected. Therefore, in special cases, it is possible to go above or below the aforementioned concentration ranges and amounts per unit area.

The following illustrate, without limitation, examples of formulations which may be used in accordance with the present invention.

FORMULATION A

5% by weight of instant compound (5), and 95% by weight of a mixture of talc and clay (3:1) are formulated into a dust by mixing and crushing. It is applied as is by dusting to weeds and/or their habitat.

FORMULATION B

20% by weight of instant compound (6), 75% by weight of a mixture of talc and clay (3:2), 3% by weight of sodium alkylbenzene sulfonate, and 2% by weight of sodium dinaphthylmethane disulfonic acid, are formulated into a wettable powder by mixing and crushing. It is diluted with water at the concentration of 1 to 500, and applied by spraying to weeds and/or their habitat.

FORMULATION C

20% by weight of instant compound (10), 75% weight of xylol, and 5% by weight of emulsifier Sorpol (trade name of the product of Toho Kagaku Kogyo K.K., Japan; polyoxyethylene alkylarylether) are formulated into an emulsifiable concentrate by mixing and stirring. It is diluted with water at the concentration of 1 to 1,000, and applied by spraying to weeds and/or their habitat.

FORMULATION D

Instant compound (20) is dissolved in xylol by heating, and the solution is sprayed onto clay granules while rotating and mixing until the granules have absorbed about 10% by weight of the active compound. The granular formulation is applied by scattering on the surface of soil.

The herbicidal effectiveness of the particular new compounds of the present invention is illustrated, without limitation, by the following Examples:

EXAMPLE 1

Test against weeds of paddy fields

Preparation of active compounds:
Carrier vehicle
    5 parts by weight of acetone or
    5 parts by weight of talc
Emulsifier
    1 part by weight of benzyloxypolyglycolether To produce a suitable preparation of the particular active compound, 1 part by weight of such active compound is mixed with the stated amount of carrier vehicle and the stated amount of emulsifier intimately, and the resulting emulsifiable concentrate or wettable powder is then diluted with water to the desired final concentration.

Test method:

Pots of 1/5,000 a. are charged with paddy field soil and then filled with water. Paddy rice seedlings (Jukkoku variety) at the three to four leaves stage are transplanted into the pots under irrigated conditions. After the seedlings have taken root, seeds of barnyard grass and broad-leaved weeds are sown and spikerush are planted in such pots simultaneously.

The preparations of the given active compound are sprayed at the rate of 500, 250 and 125 g of active compound per 10 a. onto the soil of pots. After 3 weeks, the degree of damage against barnyard grass, spikerush and broadleaved weeds and the phytotoxicity to the paddy rice are determined and characterized by the values 0 to 5, which have the following scales:

| Herbicidal efficacy | | Phytotoxicity | |
| --- | --- | --- | --- |
| 5 | Plants are completely dead | 5 | Plants are completely dead |
| 4 | Plants are partially destroyed or 20% or less germinated | 4 | Remarkable damage |
| 3 | Plants are remarkably damaged or 50 % or less germinated | 3 | Marked damage |
| 2 | Plants are markedly damaged or 70% or less germinated | 2 | Small damage |
| 1 | Plants are slightly damaged or 90% or less germinated | 1 | Slight damage |
| 0 | No effect | 0 | No phytotoxicity |

The particular active compounds tested and the results obtained can be seen from the following Table 1:

Table 1

| Active Compound No. (see Table 3) | Amount of active compound in g/10 a. | Herbicidal effect against weeds of paddy fields and phytotoxicity to rice | | | Phyto-toxicity |
| --- | --- | --- | --- | --- | --- |
| | | Herbicidal effect | | | |
| | | *Echinochloa crus-galli* (barnyard grass) | *Eleocharis acicularis* (spikerush) | broad leaved weeds | paddy rice plant |
| Compounds of Invention | | | | | |
| (1₁) | 500 | 5 | 5 | 5 | 0 |
| | 250 | 4–5 | 4 | 4 | 0 |
| | 125 | 4 | 3 | 4 | 0 |
| (2₁) | 500 | 5 | 5 | 5 | 0 |
| | 250 | 4 | 4 | 4 | 0 |
| | 125 | 4 | 4 | 4 | 0 |
| (3₁) | 500 | 5 | 5 | 5 | 0 |
| | 250 | 4 | 4 | 4–5 | 0 |
| | 125 | 4 | 3 | 4 | 0 |
| (4₁) | 500 | 5 | 5 | 5 | 0 |
| | 250 | 5 | 4–5 | 5 | 0 |
| | 125 | 4–5 | 4 | 5 | 0 |
| (5₁) | 500 | 5 | 5 | 5 | 0 |
| | 250 | 5 | 4 | 5 | 0 |
| | 125 | 4 | 3–4 | 5 | 0 |
| (6₁) | 500 | 5 | 5 | 5 | 0 |
| | 250 | 5 | 4 | 5 | 0 |
| | 125 | 4–5 | 4 | 5 | 0 |
| (7₁) | 500 | 5 | 5 | 5 | 0 |
| | 250 | 5 | 4 | 4 | 0 |
| | 125 | 4 | 3 | 3 | 0 |
| (8₁) | 500 | 5 | 4 | 4 | 0 |
| | 250 | 5 | 4 | 4 | 0 |
| | 125 | 4 | 3 | 3 | 0 |
| (9₁) | 500 | 5 | 4 | 4 | 0 |
| | 250 | 5 | 4 | 4 | 0 |
| | 125 | 4–5 | 3–4 | 4 | 0 |
| (10₁) | 500 | 5 | 5 | 5 | 0 |
| | 250 | 5 | 5 | 5 | 0 |
| | 125 | 5 | 4 | 5 | 0 |
| (11₁) | 500 | 5 | 5 | 5 | 0 |
| | 250 | 5 | 4 | 4 | 0 |
| | 125 | 4 | 3 | 4 | 0 |
| (12₁) | 500 | 5 | 5 | 5 | 0 |
| | 250 | 5 | 4 | 5 | 0 |
| | 125 | 5 | 4 | 4–5 | 0 |
| (13₁) | 500 | 5 | 5 | 5 | 0 |
| | 250 | 4–5 | 4 | 4 | 0 |
| | 125 | 4 | 3 | 3 | 0 |
| (14₁) | 500 | 5 | 5 | 5 | 0 |
| | 250 | 4–5 | 5 | 4 | 0 |
| | 125 | 4 | 4 | 4 | 0 |
| (15₁) | 500 | 5 | 5 | 5 | 0 |
| | 250 | 4 | 4 | 5 | 0 |
| | 125 | 4 | 3 | 5 | 0 |
| (16₁) | 500 | 5 | 5 | 5 | 0 |
| | 250 | 4–5 | 4 | 5 | 0 |
| | 125 | 4 | 3 | 5 | 0 |
| (17₁) | 500 | 5 | 5 | 5 | 0 |
| | 250 | 4 | 4 | 5 | 0 |
| | 125 | 4 | 3–4 | 4 | 0 |
| (18₁) | 500 | 5 | 5 | 5 | 0 |
| | 250 | 4 | 4 | 5 | 0 |
| | 125 | 4 | 4 | 4 | 0 |
| (19₁) | 500 | 5 | 5 | 5 | 0 |
| | 250 | 4 | 4 | 5 | 0 |
| | 125 | 4 | 4 | 4–5 | 0 |
| (20₁) | 500 | 5 | 5 | 5 | 0 |
| | 250 | 4–5 | 5 | 4 | 0 |
| | 125 | 4 | 4 | 3 | 0 |
| (21₁) | 500 | 5 | 5 | 5 | 0 |
| | 250 | 5 | 4–5 | 4 | 0 |
| | 125 | 4 | 4 | 3 | 0 |
| (22₁) | 500 | 5 | 5 | 5 | 0 |
| | 250 | 5 | 4 | 5 | 0 |
| | 125 | 4 | 3 | 4 | 0 |
| (23₁) | 500 | 5 | 4 | 3–4 | 0 |
| | 250 | 4 | 3 | 3 | 0 |
| | 125 | 3–4 | 3 | 3 | 0 |
| (24₁) | 500 | 5 | 4 | 4 | 0 |
| | 250 | 4 | 4 | 4 | 0 |
| | 125 | 4 | 3 | 4 | 0 |
| (25₁) | 500 | 5 | 4 | 4 | 0 |
| | 250 | 4 | 4 | 4 | 0 |
| | 125 | 4 | 4 | 4 | 0 |
| (26₁) | 500 | 5 | 5 | 5 | 0 |
| | 250 | 4–5 | 4 | 5 | 0 |
| | 125 | 4 | 4 | 5 | 0 |
| (27₁) | 500 | 5 | 4 | 4 | 0 |
| | 250 | 4 | 3 | 4 | 0 |
| | 125 | 3 | 3 | 4 | 0 |
| | 500 | 5 | 4 | 4 | 0 |

Table 1-continued

| Active Compound No. (see Table 3) | Amount of active compound in g/10 a. | Herbicidal effect against weeds of paddy fields and phytotoxicity to rice | | | Phyto- toxicity |
|---|---|---|---|---|---|
| | | Herbicidal effect | | | |
| | | *Echinochloa crus-galli* (barnyard grass) | *Eleocharis acicularis* (spikerush) | broad leaved weeds | paddy rice plant |
| ($28_1$) | 250 | 4–5 | 3 | 4 | 0 |
| | 125 | 4 | 3 | 3 | 0 |
| | 500 | 4 | 2 | 3 | 0 |
| ($29_1$) | 250 | 3–4 | 2 | 3 | 0 |
| | 125 | 3 | 2 | 3 | 0 |
| | 500 | 4 | 3 | 3 | 0 |
| ($30_1$) | 250 | 4 | 2–3 | 3 | 0 |
| | 125 | 3 | 2 | 3 | 0 |
| | 500 | 5 | 5 | 5 | 0 |
| ($31_1$) | 250 | 4–5 | 4 | 4–5 | 0 |
| | 125 | 4 | 3–4 | 3–4 | 0 |
| | 500 | 5 | 5 | 5 | 0 |
| ($32_1$) | 250 | 4–5 | 4 | 4–5 | 0 |
| | 125 | 4 | 3–4 | 3–4 | 0 |
| | 500 | 5 | 5 | 5 | 0 |
| ($33_1$) | 250 | 5 | 5 | 4 | 0 |
| | 125 | 4 | 4 | 3–4 | 0 |
| | 500 | 5 | 5 | 5 | 0 |
| ($34_1$) | 250 | 5 | 4–5 | 4–5 | 0 |
| | 125 | 4–5 | 4 | 4 | 0 |
| | 500 | 5 | 5 | 5 | 0 |
| ($35_1$) | 250 | 4–5 | 4 | 4 | 0 |
| | 125 | 4 | 4 | 4 | 0 |
| | 500 | 5 | 5 | 5 | 0 |
| ($36_1$) | 250 | 4–5 | 4–5 | 4 | 0 |
| | 125 | 4 | 4 | 4 | 0 |
| | 500 | 5 | 5 | 5 | 0 |
| ($37_1$) | 250 | 4–5 | 4 | 4 | 0 |
| | 125 | 4 | 4 | 4 | 0 |
| | 500 | 5 | 5 | 5 | 0 |
| ($38_1$) | 250 | 4–5 | 4 | 4–5 | 0 |
| | 125 | 4 | 4 | 4 | 0 |
| | 500 | 5 | 5 | 5 | 0 |
| ($39_1$) | 250 | 4–5 | 4–5 | 4–5 | 0 |
| | 125 | 4 | 4 | 4 | 0 |
| | 500 | 5 | 5 | 5 | 0 |
| ($40_1$) | 250 | 5 | 4 | 4–5 | 0 |
| | 125 | 4 | 4 | 4 | 0 |
| | 500 | 5 | 5 | 5 | 0 |
| ($41_1$) | 250 | 5 | 4–5 | 4 | 0 |
| | 125 | 4 | 4 | 3–4 | 0 |
| Known Compounds-Comparison | | | | | |
| (A) Benzyl-N,N-dimethyl dithio-carbamate | 500 | 5 | 5 | 5 | 0 |
| | 250 | 4 | 2 | 4 | 0 |
| | 125 | 2 | 1 | 2 | 0 |
| (B) Penta-chloro-phenol | 1000 | 5 | 5 | 5 | 1 |
| | 250 | 2 | 5 | 5 | 0 |
| (C) 2-methyl-4-chloro-phenoxy-acetic acid | | | | | |
| Control | — | 0 | 0 | 0 | 0 |

NOTES:
1) Broad-leaved weeds are *Rotala indica*, *Monochoria vaginalis*, *Lindernia pyxidaria*, etc.

EXAMPLE 2

Selective herbicidal effect test for barnyard grass and rice plant (pre-emergence test, direct seeding)

Test method:

A pot of 1/5,000 a. is charged with paddy field soil and supplied with water to provide irrigated condition. Seeds of barnyard grass (*Echinochloa crus-galli*) and paddy rice plant (Kinmaze variety) are sown. The particular active compound in the form of a corresponding wettable powder or emulsifiable concentrate, produced in the manner of Formulation (B) and (C) above, is sprayed on the surface of the soil at the rate of 1,000, 500 and 250 g of active compound per 10 a. of pot soil. After 3 weeks, the herbicidal effect against barnyard grass and the phytotoxicity to paddy rice plant are determined to investigate the selective herbicidal activity between barnyard grass and rice plant in accordance with the same scales as of Example 1.

The particular active compounds tested on the results obtained can be seen from the following Table 2:

Table 2

| Active Compound No. (see Table 3) | Amount of active compound (g/10 a.) | Herbicidal effect against barnyard grass and phytotoxicity to rice plant | Phytotoxicity |
|---|---|---|---|
| | | Herbicidal effect *Echinochloa crus-galli* (barnyard grass) | Rice-plant |
| Compounds of Invention | | | |
| ($1_2$) | 1000 | 5 | 2 |
| | 500 | 5 | 0 |
| | 250 | 4 | 0 |
| ($2_2$) | 1000 | 5 | 1–2 |
| | 500 | 5 | 0 |
| | 250 | 4 | 0 |
| | 1000 | 5 | 2 |

Table 2-continued

| Active Compound No. (see Table 3) | Amount of active compound (g/10 a.) | Herbicidal effect  Echinochloa crus-galli (barnyard grass) | Phytotoxicity Rice-plant |
|---|---|---|---|
| ($3_2$) | 500 | 5 | 0 |
|  | 250 | 4 | 0 |
| ($4_2$) | 1000 | 5 | 2 |
|  | 500 | 5 | 0 |
|  | 250 | 4–5 | 0 |
| ($5_2$) | 1000 | 5 | 2 |
|  | 500 | 5 | 0 |
|  | 250 | 5 | 0 |
| ($6_2$) | 1000 | 5 | 2 |
|  | 500 | 5 | 1 |
|  | 250 | 4 | 0 |
| ($7_2$) | 1000 | 5 | 2 |
|  | 500 | 5 | 1 |
|  | 250 | 4 | 0 |
| ($8_2$) | 1000 | 5 | 2 |
|  | 500 | 5 | 0 |
|  | 250 | 4–5 | 0 |
| ($9_2$) | 1000 | 5 | 1–2 |
|  | 500 | 5 | 0 |
|  | 250 | 4 | 0 |
| ($10_2$) | 1000 | 5 | 2 |
|  | 500 | 5 | 1 |
|  | 250 | 5 | 0 |
| ($11_2$) | 1000 | 5 | 2 |
|  | 500 | 5 | 1 |
|  | 250 | 5 | 0 |
| ($12_2$) | 1000 | 5 | 2 |
|  | 500 | 5 | 1 |
|  | 250 | 5 | 0 |
| ($13_2$) | 1000 | 5 | 2 |
|  | 500 | 4 | 0 |
|  | 250 | 4 | 0 |
| ($14_2$) | 1000 | 5 | 2 |
|  | 500 | 5 | 1 |
|  | 250 | 4–5 | 0 |
| ($15_2$) | 1000 | 5 | 2 |
|  | 500 | 5 | 0 |
|  | 250 | 4–5 | 0 |
| ($16_2$) | 1000 | 5 | 2 |
|  | 500 | 5 | 0 |
|  | 250 | 4 | 0 |
| ($17_2$) | 1000 | 5 | 2 |
|  | 500 | 5 | 0 |
|  | 250 | 4 | 0 |
| ($18_2$) | 1000 | 5 | 2 |
|  | 500 | 5 | 1–2 |
|  | 250 | 4 | 0 |
| ($19_2$) | 1000 | 5 | 2 |
|  | 500 | 5 | 0 |
|  | 250 | 4 | 0 |
| ($20_2$) | 1000 | 5 | 2 |
|  | 500 | 5 | 1 |
|  | 250 | 5 | 0 |
| ($21_2$) | 1000 | 5 | 2 |
|  | 500 | 5 | 1 |
|  | 250 | 5 | 0 |
| ($22_2$) | 1000 | 5 | 2 |
|  | 500 | 5 | 1 |
|  | 250 | 4 | 0 |
| ($23_2$) | 1000 | 5 | 2 |
|  | 500 | 4 | 0 |
|  | 250 | 4 | 0 |
| ($24_2$) | 1000 | 5 | 2 |
|  | 500 | 4 | 0 |
|  | 250 | 3 | 0 |
| ($25_2$) | 1000 | 5 | 2 |
|  | 500 | 4 | 1 |
|  | 250 | 3 | 0 |
| ($26_2$) | 1000 | 5 | 2 |
|  | 500 | 5 | 0 |
|  | 250 | 5 | 0 |
| ($27_2$) | 1000 | 5 | 2 |
|  | 500 | 4 | 0 |
|  | 250 | 3 | 0 |
| ($28_2$) | 1000 | 5 | 2 |
|  | 500 | 4 | 1 |
|  | 250 | 3 | 0 |
| ($29_2$) | 1000 | 4–5 | 2 |
|  | 500 | 4 | 0 |
|  | 250 | 3 | 0 |
| ($30_2$) | 1000 | 4 | 2 |
|  | 500 | 3 | 1 |
|  | 250 | 3 | 0 |
| ($31_2$) | 1000 | 5 | 2 |
|  | 500 | 4–5 | 0 |
|  | 250 | 4 | 0 |
| ($32_2$) | 1000 | 5 | 2 |
|  | 500 | 4–5 | 0 |
|  | 250 | 3 | 0 |
| ($33_2$) | 1000 | 5 | 2 |
|  | 500 | 5 | 0 |
|  | 250 | 4 | 0 |
| ($34_2$) | 1000 | 5 | 2 |
|  | 500 | 5 | 0 |
|  | 250 | 4 | 0 |
| ($35_2$) | 1000 | 5 | 0 |
|  | 500 | 4–5 | 0 |
|  | 250 | 4 | 0 |
| ($36_2$) | 1000 | 5 | 2 |
|  | 500 | 4–5 | 0 |
|  | 250 | 4 | 0 |
| ($37_2$) | 1000 | 5 | 0 |
|  | 500 | 4–5 | 0 |
|  | 250 | 4 | 0 |
| ($38_2$) | 1000 | 5 | 2 |
|  | 500 | 4–5 | 0 |
|  | 250 | 4 | 0 |
| ($39_2$) | 1000 | 5 | 2 |
|  | 500 | 4–5 | 1 |
|  | 250 | 4 | 0 |
| ($40_2$) | 1000 | 5 | 2 |
|  | 500 | 5 | 0 |
|  | 250 | 4 | 0 |
| ($41_2$) | 1000 | 5 | 2 |
|  | 500 | 5 | 0 |
|  | 250 | 4 | 0 |
| Known Compounds-Comparison | | | |
| (A) Benzyl-N,N-dimethyl-dithio-carbamate | 1000 | 5 | 5 |
|  | 500 | 4 | 2 |
|  | 250 | 3 | 0 |
| (B) Pentachlorophenol | 1000 | 5 | 5 |
|  | 500 | 5 | 5 |
|  | 250 | 2 | 1 |
| Control | — | 0 | 0 |

The following further examples illustrate, without limitation, the process for producing the particular new compounds of the present invention.

EXAMPLE 3

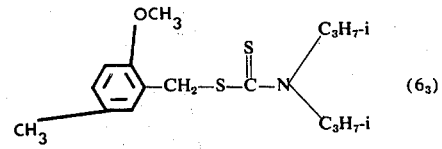

20 g. (0.1 mol) of sodium diisopropyl-dithiocarbamate is mixed with 200 ml. of methyl ethyl ketone and charged into a 500 ml. three necked flask. Then, 17 g. (0.1 mol) of 2-methoxy-5-methyl benzyl chloride dissolved in 100 ml. of methyl ethyl ketone is gradually added dropwise thereto while stirring, keeping the reaction mixture at a temperature of 80°–85°C on a water bath. After the completion of the dropwise addition, the reaction solution is continuously stirred at a temperature of 90°C for 1 hour, then cooled after the reaction has been completed. The formed precipitate is then filtered. The filtrate is concentrated under reduced pressure, cooled and allowed to stand to obtain the crude crystals.

The crude crystals are recrystallized from alcohol to obtain 26.1 g. of 2-methoxy-5-methyl-benzyl-N,N-diisopropyl-dithiocarbamate, having a melting point of 136°–136.5°C.

EXAMPLE 4

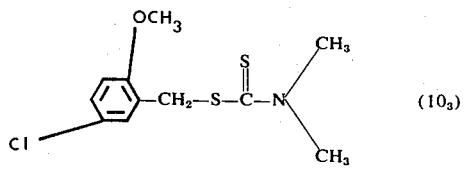

14.3 g. (0.1 mol) of sodium dimethyl-dithiocarbamate is mixed with 200 ml. of acetone, and charged into a 500 ml three necked flask. Then, 19.1 g. (0.1 mol) of 2 methoxy-5-chloro-benzyl chloride dissolved in 100 ml. of acetone is gradually added dropwise thereto under reflux on a water bath while stirring. After the completion of the dropwise addition, the reflux of the reaction solution is continued for 3 hours, then cooled after the reaction has been completed. The precipitate is then filtered. The filtrate is concentrated to obtain the crude crystals. The crude crystals are recrystallized from alcohol to obtain 23.5 g. of 2-methoxy-5-chloro-benzyl-N,N-dimethyl-dithiocarbamate, having a melting point of 128°–129°C.

In an analogous manner to Examples 3 and 4, each of the other compounds of the present invention may be prepared.

The following Table 3 illustrates appropriate data for typical compounds of the present invention.

Table 3

| Compound | Structural Formula | Chemical name | Physical property |
|---|---|---|---|
| (1₃) | | 3-methyl-4-methoxy-benzyl-N,N-dimethyl-dithio-carbamate | m.p. 92–94°C |
| (2₃) | | 3-methyl-4-methoxy-benzyl-N,N-diethyl-dithio-carbamate | m.p. 44–44.5°C |
| (3₃) | | 3-methyl-4-methoxy-benzyl-N,N-diiso-propyl-dithio-carbamate | m.p. 89–90°C |
| (4₃) | | 2-methoxy-5-methyl-benzyl-N,N-dimethyl-dithiocarbamate | m.p. 76–77°C |
| (5₃) | | 2-methoxy-5-methyl-benzyl-N,N-di-ethyl-dithiocarbamate | m.p. 177–178°C |
| (6₄) | | 2-methoxy-5-methyl-benzyl-N,N-diiso-propyl-dithio-carbamate | m.p. 136–136.5°C |
| (7₃) | | 3-chloro-4-methoxy-benzyl-N,N-diethyl-dithiocarbamate | m.p. 119–120°C |

Table 3-continued

| Compound | Structural Formula | Chemical name | Physical property |
|---|---|---|---|
| (8₃) | 3-chloro-4-methoxy-benzyl-S-C(=S)-N(CH₃)₂ | 3-chloro-4-methoxy-benzyl-N,N-dimethyl-dithiocarbamate | m.p. 75–76°C |
| (9₃) | 3-chloro-4-methoxy-benzyl-S-C(=S)-N(i-C₃H₇)₂ | 3-chloro-4-methoxy-benzyl-N,N-diisopropyl-dithiocarbamate | m.p. 91–92°C |
| (10₄) | 2-methoxy-5-chloro-benzyl-S-C(=S)-N(CH₃)₂ | 2-methoxy-5-chloro-benzyl-N,N-dimethyl-dithiocarbamate | m.p. 128–129°C |
| (11₃) | 2-methoxy-5-chloro-benzyl-S-C(=S)-N(C₂H₅)₂ | 2-methoxy-5-chloro-benzyl-N,N-diethyl-dithiocarbamate | m.p. 52–53°C |
| (12₃) | 2-methoxy-5-chloro-benzyl-S-C(=S)-N(i-C₃H₇)₂ | 2-methoxy-5-chloro-benzyl-N,N-diisopropyl-dithiocarbamate | m.p. 103–104°C |
| (13₃) | 2-methoxy-5-chloro-benzyl-S-C(=S)-N(CH₃)(n-C₄H₉) | 2-methoxy-5-chloro-benzyl-N-methyl-N-n-butyl-dithiocarbamate | m.p. 66–67.5°C |
| (14₃) | 2-ethoxy-5-chloro-benzyl-S-C(=S)-N(CH₃)₂ | 2-ethoxy-5-chloro-benzyl-N,N-dimethyl-dithiocarbamate | m.p. 128–130°C |
| (15₃) | 2-ethoxy-5-chloro-benzyl-S-C(=S)-N(i-C₃H₇)₂ | 2-ethoxy-5-chloro-benzyl-N,N-diisopropyl-dithiocarbamate | m.p. 61–62.5°C |
| (16₃) | 2-ethoxy-5-methyl-benzyl-S-C(=S)-N(CH₃)₂ | 2-ethoxy-5-methyl-benzyl-N,N-dimethyl-dithio-carbamate | m.p. 64–66°C |
| (17₃) | 2-ethoxy-5-methyl-benzyl-S-C(=S)-N(C₂H₅)₂ | 2-ethoxy-5-methyl-benzyl-N,N-diethyl-dithio-carbamate | m.p. 45–47°C |

Table 3-continued

| Compound | Structural Formula | Chemical name | Physical property |
|---|---|---|---|
| (18₃) | 2-ethoxy-5-methylbenzyl, OC₂H₅ and CH₃ on ring, –CH₂–S–C(=S)–N(C₃H₇-i)₂ | 2-ethoxy-5-methyl-benzyl-N,N-diisopropyl-dithiocarbamate | m.p. 90–92°C |
| (19₃) | 2-isopropoxy-5-methylbenzyl, OC₃H₇-i and CH₃ on ring, –CH₂–S–C(=S)–N(CH₃)₂ | 2-isopropoxy-5-methyl-benzyl-N,N-dimethyl-dithiocarbamate | m.p. 23–25°C |
| (20₃) | 2-methoxy-5-bromobenzyl, OCH₃ and Br on ring, –CH₂–S–C(=S)–N(CH₃)₂ | 2-methoxy-5-bromo-benzyl-N,N-dimethyl-dithiocarbamate | m.p. 151–152.5°C |
| (21₃) | 2-methoxy-3,5-dichlorobenzyl, OCH₃ and 2 Cl on ring, –CH₂–S–C(=S)–N(CH₃)₂ | 2-methoxy-3,5-dichloro-benzyl-N,N-dimethyl-dithiocarbamate | m.p. 47–58°C |
| (22₃) | 2-methoxy-3,6-dichlorobenzyl, OCH₃ and 2 Cl on ring, –CH₂–S–C(=S)–N(CH₃)₂ | 2-methoxy-3,6-dichloro-benzyl-N,N-dimethyl-dithiocarbamate | n.p. 61–63°C |
| (23₃) | 3-nitro-4-methoxybenzyl, NO₂ and CH₃O on ring, –CH₂–S–C(=S)–N(CH₃)₂ | 3-nitro-4-methoxy-benzyl-N,N-dimethyl-dithiocarbamate | m.p. 104–105°C |
| (24₃) | 3-nitro-4-methoxybenzyl, NO₂ and CH₃O on ring, –CH₂–S–C(=S)–N(C₂H₅)₂ | 3-nitro-4-methoxy-benzyl-N,N-diethyl-dithiocarbamate | m.p. 58–59°C |
| (25₃) | 3-nitro-4-methoxybenzyl, NO₂ and CH₃O on ring, –CH₂–S–C(=S)–N(C₃H₇-i)₂ | 3-nitro-4-methoxy-benzyl-N,N-diisopropyl-dithiocarbamate | m.p. 99–100°C |
| (26₃) | 2-methoxy-3-nitrobenzyl (OCH₃ and NO₂ on ring), –CH₂–S–C(=S)–N(CH₃)₂ | 2-methoxy-3-nitro-benzyl-N,N-dimethyl-dithiocarbamate | m.p. 97–99°C |
| (27₃) | 3,4-dimethoxybenzyl, CH₃O and CH₃O– on ring, –CH₂–S–C(=S)–N(CH₃)₂ | 3,4-dimethoxy-benzyl-N,N-dimethyl-dithiocarbamate | m.p. 27–29°C |

Table 3-continued

| Compound | Structural Formula | Chemical name | Physical property |
|---|---|---|---|
| (28₃) | 3,4-dimethoxybenzyl-S-C(=S)-N(C₃H₇-i)₂ | 3,4-dimethoxy-benzyl-N,N-diisopropyl-dithiocarbamate | m.p. 33–35°C |
| (29₃) | 3-chloro-4-methoxybenzyl-S-C(=S)-NH(CH₃) | 3-chloro-4-methoxy-benzyl-N-methyl-dithiocarbamate | m.p. 82–83°C |
| (30₃) | 3-chloro-4-methoxybenzyl-S-C(=S)-NH(C₂H₅) | 3-chloro-4-methoxy-benzyl-N-ethyl-dithiocarbamate | m.p. 46–47°C |
| (31₃) | 3-isopropyl-4-methoxybenzyl-S-C(=S)-N(C₃H₇-i)₂ | 3-isopropyl-4-methoxy-benzyl-N,N-diisopropyl-dithiocarbamate | m.p. 66–67°C |
| (32₃) | 2-methoxy-6-ethylbenzyl-S-C(=S)-N(CH₃)₂ | 2-methoxy-6-ethyl-benzyl-N,N-dimethyl-dithiocarbamate | m.p. 63–64°C |
| (33₃) | 3-chloro-4-ethoxybenzyl-S-C(=S)-N(C₂H₅)₂ | 3-chloro-4-ethoxy-benzyl-N,N-diethyl-dithiocarbamate | m.p. 66–67°C |
| (34₃) | 3-chloro-4-isopropoxybenzyl-S-C(=S)-N(C₃H₇-n)₂ | 3-chloro-4-isopropoxy-benzyl-N,N-di-n-propyl-dithiocarbamate | m.p. 41–42°C |
| (35₃) | 3-bromo-4-methoxybenzyl-S-C(=S)-N(CH₃)₂ | 3-bromo-4-methoxy-benzyl-N,N-dimethyl-dithiocarbamate | m.p. 127–129°C |
| (36₃) | 3-bromo-4-methoxybenzyl-S-C(=S)-N(C₃H₇-i)₂ | 3-bromo-4-methoxy-benzyl-N,N-diisopropyl-dithiocarbamate | m.p. 71–72°C |
| (37₃) | 2-methoxy-4,5-dimethylbenzyl-S-C(=S)-N(CH₃)₂ | 2-methoxy-4,5-dimethyl-benzyl-N,N-dimethyl-dithiocarbamate | m.p. 167–169°C |

Table 3-continued

| Compound | Structural Formula | Chemical name | Physical property |
|---|---|---|---|
| (38₃) | CH₃–[benzene with OCH₃]–CH₂–S–C(=S)–N(C₃H₇-i)(C₃H₇-i), with CH₃ | 2-methoxy-4,5-dimethyl-benzyl-N,N-diisopropyl-dithiocarbamate | m.p. 139–141°C |
| (39₃) | [benzene with CH₃, OCH₃, CH₃]–CH₂–S–C(=S)–N(CH₃)(CH₃) | 2-methoxy-3,5-dimethyl-benzyl-N,N-dimethyl-dithiocarbamate | m.p. 60–62°C |
| (40₃) | CH₃O–[benzene with CH₃, CH₃]–CH₂–S–C(=S)–N(C₂H₅)(C₂H₅) | 4-methoxy-2,5-dimethyl-benzyl-N,N-diethyl-dithiocarbamate | m.p. 96–97°C |
| (41₃) | i-C₃H₇O–[benzene with Cl]–CH₂–S–C(=S)–N(CH₃)(C₄H₉-n) | 2-chloro-4-isopropoxy-benzyl-N-methyl-N-n-butyl-dithiocarbamate | m.p. 47–48°C |

It will be realized by the artisan that all of the foregoing compounds contemplated by the present invention possess the desired selective or total heribicidal properties, and especially the capability of selectively destroying weeds, as well as a comparatively low toxicity toward warm-blooded creatures and a concomitantly low phytotoxicty with respect to higher plants, enabling such compounds to be used with correspondingly favorable compatibility with respect to warm-blooded creatures and higher plants for more effective control and/or elimination of weeds by selective application of such compounds to such weeds and/or their habitat. Nevertheless, the instant compounds possess total herbicidal action when used in large quantities, although selective herbicidal action is obtained when used in smaller quantities. As contemplated herein, the term "weeds" is meant to include not only weeds in the narrow sense, but also in the broad sense, whereby to cover all plants and vegetation considered undesirable for the particular purpose in question.

It will be appreciated that the instant specification and examples are set forth by way of illustration and not limitation, and that various modifications and changes may be made without departing from the spirit and scope of the present invention.

What is claimed is:

1. Alkoxy-substituted benzyl dithiocarbamate selected from the group consisting of 2-methoxy-5-methyl-benzyl-N,N-dimethyldithiocarbamate, 2-methoxy-5-chlorobenzyl-N,N-dimethyldithiocarbamate, 4-isopropoxy-3-chlorobenzyl-N, N-di-n-propyldithiocarbamate -chlorobenzyl-N,N-di-n-propyldithiocarbamate 3-chloro-4-ethoxybenzyl-N,N-diethyldithiocarbamate.

2. Compound according to claim 1 wherein such compound is 2-methoxy-5-methyl-benzyl-N,N-dimethyl-dithiocarbamate of the formula

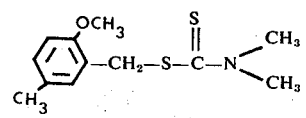

3. Compound according to claim 1 wherein such compound is 2-methoxy-5-chloro-benzyl-N,N-dimethyl-dithiocarbamate of the formula

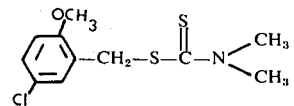

4. Compound according to claim 1 wherein such compound is 3-chloro-4-ethoxy-benzyl-N,N-diethyl-dithiocarbamate of the formula
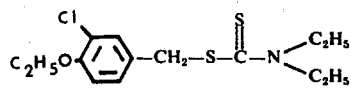
5. Compound according to claim 1 wherein such compound is 3-chloro-4-isopropoxy-benzyl-N,N-di-n-propyl-dithiocarbamate of the formula
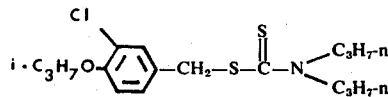
* * * * *